US008652784B2

(12) United States Patent
Zhang et al.

(10) Patent No.: US 8,652,784 B2
(45) Date of Patent: *Feb. 18, 2014

(54) DNA RECOMBINATION JUNCTION DETECTION

(75) Inventors: Jian Ping Zhang, Moraga, CA (US); Ernest Jay Friedlander, San Francisco, CA (US); Robert Ruhfel, San Francisco, CA (US); David Douglas Swenson, Santa Clara, CA (US); Alan Thomas Wortman, Redwood City, CA (US)

(73) Assignee: Cepheid, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/455,875

(22) Filed: Apr. 25, 2012

(65) Prior Publication Data
US 2013/0065774 A1 Mar. 14, 2013

Related U.S. Application Data

(62) Division of application No. 11/803,102, filed on May 11, 2007, now Pat. No. 8,187,812.

(60) Provisional application No. 60/800,104, filed on May 12, 2006.

(51) Int. Cl.
*C12Q 1/68* (2006.01)
*C12P 19/34* (2006.01)

(52) U.S. Cl.
USPC ........................................ 435/6.12; 435/91.2

(58) Field of Classification Search
None
See application file for complete search history.

(56) References Cited

U.S. PATENT DOCUMENTS

| 5,912,145 | A | 6/1999 | Stanley |
| 6,156,507 | A | 12/2000 | Hiramatsu et al. |
| 7,449,289 | B2 | 11/2008 | Huletsky et al. |
| 7,838,221 | B2 | 11/2010 | Huletsky et al. |
| 8,187,812 | B2 * | 5/2012 | Zhang et al. ............ 435/6.12 |
| 2004/0091905 | A1 | 5/2004 | Guo |
| 2008/0227087 | A1 | 9/2008 | Huletsky et al. |

FOREIGN PATENT DOCUMENTS

| EP | 0887424 A2 | 12/1998 |
| WO | 02/44407 A2 | 6/2002 |
| WO | 2007/106534 A2 | 9/2007 |
| WO | 2007/106534 A3 | 11/2008 |

OTHER PUBLICATIONS

Desjardins, M. et al.; "Evaluation of the IDI-MRSA Assay for Detection of Methicillin-Resistant *Staphylococcus aureus* from Nasal and Rectal Spectal Specimens Pooled in a Selective Broth"; 2006, *Journal of Clinical Microbiology*, vol. 44, No. 4, pp. 1219-1223.

Grisold, Andrea J. et al.; "Detection of Methicillin-Resistant *Staphylococcus aureus* and Simultaneous Confirmation by Automated Nuclecic Acid Extraction and Real-Time PCR"; 2002, *Journal of Clinical Microbiology*, vol. 40, No. 7, pp. 2392-2397.
Ito, Teruyo et al.; "Structural Comparison of Three Types of Staphylococcal Cassette Chromosome *mec* Integrated in the Chromosome in Methicillin-Resistant *Staphylococcus aureus*"; 2001, *Antimicrobial Agents and Chemotherapy*, vol. 45, No. 5, pp. 1323-1336.
Lin, Mei-Hui et al.; "Real-time PCR for rapid genotyping of angiotensin-converting enzyme insertion/deletion polymorphism"; 2001, *Clinical Biochemistry*, vol. 34, No. 8, pp. 661-666.
Mack, Kerri et al.; "The detection of insertion sequences within the human pathogen Burkholder pseudomallei which have been identified previously in *Burkholderia cepacia*"; 1998, *FEMS Microbiology Letters*, vol. 162, No. 1, pp. 6974.
Robledo, R. et al.; "A simple and cost-effective method for rapid genotyping of insertion/deletion polymorphisms"; 2003, *Genomics*, vol. 82, No. 5, pp. 580-582.
Sinsimer, Daniel et al.; "Use of a Multiplex Molecular Beacon Platform for Rapid Detection of Methicillin and Vancomycin Resistance in *Staphylococcus aureus*"; 2005, *Journal of Clinical Microbiology*, vol. 43, pp. 4585-4591.
Warren, David K. et al.; "Detection of Methicillin-Resistant *Staphylococcus aureus* Directly from Nasal Swab Specimens by a Real-Time PCR Assay"; 2004, *Journal of Clinical Microbiology*, vol. 42, No. 12, pp. 5578-5581.
International Search Report (A3 publication) of PCT/CA02/00824, filed Jun. 4, 2002. WO 02/099034 A3 published on Nov. 6, 2003, 11 pages.
International Search Report (A3 publication) of PCT/US06/39996, filed Oct. 10, 2006. WO 07/044873 A3 published on Jan. 17, 2008, 5 pages.
Huletsky et al.; "New Real-Time PCR Assay for Rapid Detection of Methicillin-Resistant *Staphylococcus aureus* Directly from Specimens Containing a Mixture of Staphylococci"; 2004; *J. Clin. Microbiol.*; 42(5): 1875-1884.
Katayama et al., "A New Class of Genetic Element, *Staphylococcus* Cassette Chromosome mec, Encodes Methicillin Resistance in *Staphylococcus aureus*," Antimicrobial Agents & Chemotherapy (2000) 44(6): 1549-1555.
Peano et al. "Multiplex polymerase chain reaction and ligation detection reaction/universal array technology for the traceability of genetically modiWed organisms in foods." Analytical Biochemistry (2005) 346: 90-100.
Kyger et al. "Detection of the Hereditary Hemochromatosis Gene Mutation by Real-Time Fluorescence Polymerase Chain Reaction and Peptide Nucleic Acid Clamping." Analytical Biochemistry (1998) 260: 142-148.
Orum et al. "Single base pair mutation analysis by PNA directed PCR clamping." Nucleic Acids Research (1993) 21(23): 5332-5336.
Murdock et al. "The age-related accumulation of a mitochondrial DNA control region mutation in muscle, but not in brain, detected by a sensitive PNA directed PCR clamping method." Nucleic Acids Research (2000) 28(21 ): 4350-4355.

* cited by examiner

*Primary Examiner* — Angela M Bertagna
(74) *Attorney, Agent, or Firm* — Kilpatrick Townsend & Stockton LLP

(57) ABSTRACT

The present invention provides methods, compositions and kits for detecting the presence or absence of an integrated insertion polynucleotide.

14 Claims, 5 Drawing Sheets

SEQUENCE LISTING

```
<160> NUMBER OF SEQ ID NOS: 17

<210> SEQ ID NO 1
<211> LENGTH: 22
<212> TYPE: DNA
<213> ORGANISM: Artificial Sequence
<220> FEATURE:
<223> OTHER INFORMATION: target Staphylococcus orfX PCR second forward
      primer (F1)

<400> SEQUENCE: 1
agggcaaagc gactttgtat tc                                             22

<210> SEQ ID NO 2
<211> LENGTH: 22
<212> TYPE: DNA
<213> ORGANISM: Artificial Sequence
<220> FEATURE:
<223> OTHER INFORMATION: target Staphylococcus orfX PCR first reverse
      primer (R11)

<400> SEQUENCE: 2
```
cttatgatac gcttctcctc gc                                            22

<210> SEQ ID NO 3
<211> LENGTH: 40
<212> TYPE: DNA
<213> ORGANISM: Artificial Sequence
<220> FEATURE:
<223> OTHER INFORMATION: Staphylococcus orfX blocker polynucleotide
      straddling an attB integration site

<400> SEQUENCE: 3
cagaattttt tagttttact tatgatacgc ctctcctcgc                          40

<210> SEQ ID NO 4
<211> LENGTH: 40
<212> TYPE: DNA
<213> ORGANISM: Artificial Sequence
<220> FEATURE:
<223> OTHER INFORMATION: Staphylococcus orfX blocker polynucleotide
      straddling an attB integration site

<400> SEQUENCE: 4
taaaaaactc ctccgctact tatgatacgc ttctcctcgc                          40

<210> SEQ ID NO 5
<211> LENGTH: 30
<212> TYPE: DNA
<213> ORGANISM: Artificial Sequence
<220> FEATURE:
<223> OTHER INFORMATION: Staphylococcus orfX amplicon PCR detectable
      probe

<400> SEQUENCE: 5
cggcctgcac aaggacgtct tacaacgtag                                    30

<210> SEQ ID NO 6
<211> LENGTH: 49
<212> TYPE: DNA
<213> ORGANISM: Artificial Sequence
<220> FEATURE:
<223> OTHER INFORMATION: Staphylococcus orfX blocker polynucleotide
      Blocker-GCG49 straddling an attB integration site

<400> SEQUENCE: 6
ctcctcatac agaattttt agttttactt atgatacgcc tctcctcgc                49

<210> SEQ ID NO 7
<211> LENGTH: 55
<212> TYPE: DNA
<213> ORGANISM: Artificial Sequence
<220> FEATURE:
<223> OTHER INFORMATION: Staphylococcus orfX blocker polynucleotide
      Blocker-CTA55 straddling an attB integration site

<400> SEQUENCE: 7
ctcctcatac agaattttt agttttactt atgatacgcc tctccacgca taatc         55

<210> SEQ ID NO 8
<211> LENGTH: 63
<212> TYPE: DNA
<213> ORGANISM: Artificial Sequence
<220> FEATURE:
<223> OTHER INFORMATION: Staphylococcus orfX blocker polynucleotide
      Blocker-CGT63 straddling an attB integration site

<400> SEQUENCE: 8
ctcctcatac agaattttt agttttactt atgatacgcc tctccacgca taatcttaaa   60
tgc                                                              63

<210> SEQ ID NO 9
<211> LENGTH: 29
<212> TYPE: DNA
<213> ORGANISM: Artificial Sequence
<220> FEATURE:
<223> OTHER INFORMATION: Staphylococcus orfX PCR first reverse primer

<400> SEQUENCE: 9
gcttctccac gcataatctt aaatgctct                                  29

<210> SEQ ID NO 10
<211> LENGTH: 20
<212> TYPE: DNA
<213> ORGANISM: Artificial Sequence
<220> FEATURE:
<223> OTHER INFORMATION: Staphylococcus orfX PCR first reverse primer R6

<400> SEQUENCE: 10
tacttatgat acgcttctcc                                            20

<210> SEQ ID NO 11
<211> LENGTH: 10
<212> TYPE: DNA
<213> ORGANISM: Artificial Sequence
<220> FEATURE:
<223> OTHER INFORMATION: 1-10 consecutive cytosine or guanosine bases
      preceding hybridizing region at the 5'-end of
      first and/or second primer
<221> NAME/KEY: modified_base
<222> LOCATION: (2)...(10)
<223> OTHER INFORMATION: c or g base may be present or absent

<400> SEQUENCE: 11 ssssssssss                                                       10

<210> SEQ ID NO 12
<211> LENGTH: 40
<212> TYPE: DNA
<213> ORGANISM: Artificial Sequence
<220> FEATURE:
<223> OTHER INFORMATION: Staphylococcus orfX blocker polynucleotide
      straddling an attB integration site
<221> NAME/KEY: modified_base
<222> LOCATION: (40)...(40)
<223> OTHER INFORMATION: n = c modified by 3' phosphate (PO-3) blocking
      moiety

<400> SEQUENCE: 12
cagaattttt tagttttact tatgatacgc ctctcctcgn                      40

<210> SEQ ID NO 13
<211> LENGTH: 40
<212> TYPE: DNA
<213> ORGANISM: Artificial Sequence
<220> FEATURE:
<223> OTHER INFORMATION: Staphylococcus orfX blocker polynucleotide
      straddling an attB integration site
<221> NAME/KEY: modified_base
<222> LOCATION: (40)...(40)
<223> OTHER INFORMATION: n = c modified by 3' phosphate (PO-3) blocking
      moiety

<400> SEQUENCE: 13
taaaaaactc ctccgctact tatgatacgc ttctcctcgn                      40

<210> SEQ ID NO 14

```
<211> LENGTH: 30
<212> TYPE: DNA
<213> ORGANISM: Artificial Sequence
<220> FEATURE:
<223> OTHER INFORMATION: Staphylococcus orfX amplicon FAM-labeled PCR
      amplification detection probe
<221> NAME/KEY: modified_base
<222> LOCATION: (1)...(1)
<223> OTHER INFORMATION: n = c modified by 5' fluorescein (FAM)
<221> NAME/KEY: modified_base
<222> LOCATION: (30)...(30)
<223> OTHER INFORMATION: n = g modified by 3' quencher (Q; e.g., QSY7)

<400> SEQUENCE: 14
nggcctgcac aaggacgtct tacaacgtan                                    30

<210> SEQ ID NO 15
<211> LENGTH: 139
<212> TYPE: DNA
<213> ORGANISM: Artificial Sequence
<220> FEATURE:
<223> OTHER INFORMATION: methicillin-sensitive Staphylococcus aureus
      (MSSA) strain ATCC 35556 target blocker region

<400> SEQUENCE: 15
attatctcct catacagaat tttttagttt tacttatgat acgcctctcc tcgcataatc   60
ttaaatgctc tgtacacttg ttcaattaac acaacccgca tcatttgatg tgggaatgtc  120
attttgctga atgaagtgc                                              139

<210> SEQ ID NO 16
<211> LENGTH: 33
<212> TYPE: DNA
<213> ORGANISM: Artificial Sequence
<220> FEATURE:
<223> OTHER INFORMATION: methicillin-sensitive Staphylococcus aureus
      (MSSA) strain ATCC 35556 PCR Probe M180

<400> SEQUENCE: 16
ccccgcttct ccacgcataa tcttaaatgc tct                               33

<210> SEQ ID NO 17
<211> LENGTH: 32
<212> TYPE: DNA
<213> ORGANISM: Artificial Sequence
<220> FEATURE:
<223> OTHER INFORMATION: methicillin-sensitive Staphylococcus aureus
      (MSSA) strain ATCC 35556 PCR Primer

<400> SEQUENCE: 17
caattaacac aacccgcatc atttgatgtg gg                                32
```

DNA RECOMBINATION JUNCTION DETECTION

CROSS-REFERENCE TO RELATED PATENT APPLICATIONS

This patent application is a divisional of U.S. application Ser. No. 11/803,102, filed May 11, 2007, now U.S. Pat. No. 8,187,812, which claims the benefit of U.S. Provisional Patent Application No. 60/800,104, filed May 12, 2006, the entire disclosures of which are hereby incorporated herein by reference for all purposes.

BACKGROUND OF THE INVENTION

Detection of integrated insertion nucleotide sequences is important in many contexts. For example, insertion nucleotide sequences can transport oncogenes in mammals, antibiotic resistance genes in bacteria and genes conveying identifiable traits in plants. Bacterial antibiotic resistance is a major worldwide clinical problem and public health concern (see, for example, Sheldon, *Clin Lab Sci* (2005) 18:170 and French, *Adv Drug Deliv Rev* (2005) 57:1514). Clearly, an efficient, sensitive and reliable method for detecting the presence or absence of an integrated insertion nucleotide is valuable in clinical diagnostics and other contexts.

Others have developed methods for detecting integrated insertion nucleotide sequences. In one approach, the integrated insertion nucleotide is detected using PCR where one primer hybridizes to the target nucleic acid sequence and the other primer hybridizes to the insertion nucleotide. Positive detection of the amplicon indicates the presence of an insertion polynucleotide. This method can result in false negatives, or undetected insertion nucleotides, because the sequences of insertion nucleotides are often variable. Available primers may or may not hybridize to the insertion polynucleotide. See, for example, the IDI-MRSAT™ Test by GeneOhm Sciences, San Diego, Calif.

In another approach, the integrated insertion nucleotide is detected using PCR where both primers hybridize to the insertion polynucleotide. Again, positive detection of amplicon indicates the presence of an integrated insertion polynucleotide. This method also has the shortcoming that is can result in false negatives, due to the polymorphic nature of integrated insertion nucleotides. Also, it is not clear whether the insertion polynucleotide is integrated into the target nucleic acid sequence when both forward and reverse primers hybridize to the insertion polynucleotide. See, for example, Kreiswirth, et al., *J Clin Microbiol* (2005) 43:4585 and LightCycler® MRSA Detection Kit by Roche Diagnostics, Alameda, Calif.

In a further approach, presence or absence of the integrated insertion polynucleotide is identified using PCR where one primer hybridizes to the target nucleic acid sequence and the other primer hybridizes to a sequence straddling the integration site between the target nucleic acid sequence and the insertion polynucleotide. Here, negative detection (lack of amplification) of amplicon indicates the presence of an integrated insertion polynucleotide. This method has the disadvantage that a negative signal indicates the positive integration of an insertion polynucleotide (see, U.S. Pat. No. 6,156,507).

There remains a need for efficient, sensitive methods for detecting integrated insertion polynucleotides which provide a positive signal indicative of the integration of the insertion polynucleotide.

BRIEF SUMMARY OF THE INVENTION

The present invention provides compositions (e.g., solutions, reaction mixtures), methods and kits for detecting the presence or absence of an insertion polynucleotide in a nucleic acid. The compositions, methods and kits find use in detecting, for example, integrated insertion polynucleotides that confer resistance in bacteria to antibiotics.

With respect to the methods, the invention provides methods for determining the presence or absence of an integrated insertion polynucleotide at a junction site in a target polynucleotide sequence. In some embodiments, the methods comprise contacting the target polynucleotide with a first primer, a second primer, a blocker polynucleotide, a polymerase, and one or more nucleotide triphosphates, wherein:

(i) the target polynucleotide comprises a polynucleotide strand comprising a junction site that, when an integrated insertion polynucleotide is absent, is spanned on one side by a first target sequence and on the other side by a second target sequence that is contiguous with the first target sequence, (ii) the blocker polynucleotide hybridizes to the contiguous first and second target sequences when the integrated insertion polynucleotide is absent, (iii) the first primer hybridizes to a first region of the first target sequence that is proximal to the junction site, such that (iv) the second primer hybridizes to a second region of the first target sequence that is distal to the junction site, wherein the second primer is capable of priming synthesis of a copy of the first target sequence that comprises the first and second regions of the first target sequence, such that when an integrated insertion sequence is present at the junction site, the first and second primers support exponential amplification of the first and second regions of the first target sequence, and when an integrated insertion sequence is absent from the junction site, the blocker polynucleotide hybridizes to the contiguous first and second target sequences so that amplification of the first and second regions of the first target sequence is inhibited, whereby the presence or absence of the integrated insertion polynucleotide at the junction site in the target polynucleotide is determined.

With respect to the compositions, the invention provides compositions, including reaction mixtures and solutions for determining the presence or absence of an integrated insertion polynucleotide at a junction site of a first target sequence and a second target sequence in a target polynucleotide. In some embodiments, the compositions comprise the target polynucleotide, a first primer, a second primer and a blocker polynucleotide, wherein:

(i) the target polynucleotide comprises a polynucleotide strand comprising a junction site that, when an integrated insertion polynucleotide is absent, is spanned on one side by a first target sequence and on the other side by a second target sequence that is contiguous with the first target sequence, (ii) the blocker polynucleotide hybridizes to the contiguous first and second target sequences when the integrated insertion polynucleotide is absent, (iii) the first primer hybridizes to a first region of the first target sequence that is proximal to the junction site, such that (iv) the second primer hybridizes to a second region of the first target sequence that is distal to the junction site, wherein the second primer is capable of priming synthesis of a copy of the first target sequence that comprises the first and second regions of the first target sequence, such that when an integrated insertion sequence is present at the junction site, the first and second primers support exponential amplification of the first and second regions of the first target sequence, and when an integrated insertion sequence is absent from the junction site, the blocker polynucleotide hybridizes to the contiguous first and second target sequences so that amplification of the first and second regions of the first target sequence is inhibited.

With respect to the kits, the invention provides kits for determining the presence or absence of an integrated insertion polynucleotide at a junction site of a first target sequence and a second target sequence in a target polynucleotide. In some embodiments, the kits comprise a first primer, a second primer and a blocker polynucleotide, wherein:

(i) the target polynucleotide comprises a polynucleotide strand comprising a junction site that, when an integrated insertion polynucleotide is absent, is spanned on one side by a first target sequence and on the other side by a second target sequence that is contiguous with the first target sequence, (ii) the blocker polynucleotide hybridizes to the contiguous first and second target sequences when the integrated insertion polynucleotide is absent, (iii) the first primer hybridizes to a first region of the first target sequence that is proximal to the junction site, such that (iv) the second primer hybridizes to a second region of the first target sequence that is distal to the junction site, wherein the second primer is capable of priming synthesis of a copy of the first target sequence that comprises the first and second regions of the first target sequence, such that when an integrated insertion sequence is present at the junction site, the first and second primers support exponential amplification of the first and second regions of the first target sequence, and when an integrated insertion sequence is absent from the junction site, the blocker polynucleotide hybridizes to the contiguous first and second target sequences so that amplification of the first and second regions of the first target sequence is inhibited.

With respect to further embodiments of the methods, compositions and kits, in some embodiments, the full length of the first primer hybridizes to the first target sequence competitively with the blocker. In some embodiments, a portion of the first primer hybridizes to the first target sequence competitively with the blocker.

In some embodiments, first region of the first target sequence is outside the region of inverted repeats that can exist near a junction or integration site. In some embodiments, first region of the first target sequence is at least 20, 30, 40 or more nucleotide bases from the junction site.

In some embodiments, the first primer and the blocker polynucleotide each are substantially complementary to the first region within the target polynucleotide and the first primer has fewer mismatched nucleotides than the blocker polynucleotide relative to the first region within the target polynucleotide. In some embodiments, the first primer is completely complementary to the first region within the target polynucleotide and the blocker polynucleotide carries at least one internal mismatch compared to the first region of the target polynucleotide.

In some embodiments, the first target sequence and the second target sequence are portions of the *Staphylococcus aureus* orfX, the junction site is an attB integration site, the insertion polynucleotide is at least a portion of a SCCmec complex, and the target polynucleotide is DNA from *Staphylococcus aureus*.

In some embodiments, the blocker is not extendable. In some embodiments, the blocker polynucleotide comprises a moiety at its 3'-end selected from the group consisting of phosphate and hexylamine. In some embodiments, the blocker polynucleotide comprises at least one nucleic acid analog base.

In some embodiment, the nucleotide triphosphates are dNTP nucleotides.

In some embodiments, the polymerase is a DNA polymerase, for example, a Taq polymerase.

The methods, compositions and kits can be designed for the simultaneous evaluation of multiple target polynucleotides for the presence or absence of an integrated insertion polynucleotide. In some embodiments, the methods are performed in a multiplex format.

In some embodiments, the methods further comprise the step of exposing, the reaction mixture or target polynucleotide to amplification conditions. In some embodiments, the amplification is by PCR. In some embodiments, the methods are performed by multiplex PCR. In some embodiments, the amplification is detected by real-time PCR.

In some embodiments, the insertion polynucleotide is at least 10 nucleotide bases in length. In some embodiments, the insertion polynucleotide is integrated in the junction site. In some embodiments, the insertion polynucleotide is not integrated in the junction site.

In some embodiments, the kits further comprise a control target polynucleotide comprising the first target sequence and second target sequence.

DEFINITIONS

An "insertion polynucleotide" or "insertion sequence" interchangeably refer to a polynucleotide that is not natively located at a particular insertion site, but can be inserted within and become a contiguous sequence within the target polynucleotide sequence. The insertion polynucleotide can originate from another place in the same sequence (e.g., transposons), or come from the genome of another organism (e.g., a virus). An integrated insertion polynucleotide can be transmitted by an organism to its progeny. Non-limiting examples of insertion polynucleotides include transposons, mobile genetic elements and retroviral vectors. Integration of the insertion polynucleotide can but need not result in a detectable phenotype. For example, an insertion polynucleotide can also include a nucleic acid sequence that confers antibiotic resistance in bacteria. An insertion polynucleotide can also be created by a DNA translocation event (e.g., a translocational tumor marker, including c-erb-B2 RNA splice variants; bcr-lab1 fusion; and translocations affecting Bcl-2 or Bcl-10) or can be any other marker junction created by a DNA recombination event. See, FIGS. 1 and 2.

"Junction" or "junction site" interchangeably refer to a site at which the first target sequence abuts the second target sequence in a target polynucleotide sequence. A junction is also referred to as an integration site. An insertion sequence is inserted into the target polynucleotide sequence at the junction or integration site. See, FIGS. 1 and 2.

"Spanning the junction" refers to the ability of a polynucleotide to hybridize to two polynucleotides forming a junction by hybridizing to the 5'-end of one polynucleotide and the 3'-end of the other polynucleotide. Polynucleotides spanning the junction of two sequences hybridize to the 3'-end of the first sequence and the 5'-end of the second sequence, wherein the 3' nucleotide of the first sequence and the 5' nucleotide of the second sequence are immediately adjacent to each other.

The terms "proximal" or "adjacent" interchangeably refers to the positioning of a region in the target polynucleotide sequence substantially complementary to and hybridizable to the first primer with respect to the junction site in the target polynucleotide sequence. The region hybridizable to the first primer and junction site can be separated by 1 to about 20 nucleotides, for example, about 1 to 10 nucleotides. In some embodiments, the region hybridizable by the first primer and junction site directly abut one another.

"Amplification conditions" or "extension conditions" interchangeably refer to conditions under which a polymerase can add nucleotides to the 3' end of a polynucleotide. Such amplification or extension conditions are well known in the art, and are described, for example, in Sambrook and Russell, *Molecular Cloning: A Laboratory Manual*, 3rd Edition, 2001, Cold Spring Harbor Laboratory Press and Ausubel, et al, *Current Protocols in Molecular Biology*, 1987-2007, John Wiley & Sons.

"Substantially complementary," as used herein, refers to a sequence having no more than 20% (e.g., no more than 15, 10 or 5%) of the nucleotides in the sequence in question mismatched with a target sequence. In some embodiments, the two polynucleotides have 1, 2, 3, 4, 5, or more nucleotide mismatches.

A "mismatched nucleotide" refers to a nucleotide in a sequence of interest that is not the complement of the corresponding nucleotide in a corresponding sequence when the sequence of interest and the target sequence are hybridized in an amplification reaction. The complement of C is G and the complement of A is T. Those of skill in the art will appreciate that a variety of synthetic nucleotides which have Watson-Crick binding properties are known and complementary synthetic nucleotides are intended to be encompassed by this definition.

A "blocker polynucleotide" refers to a polynucleotide that hybridizes to a target polynucleotide sequence that spans an integration site (i.e., junction) for an insertion polynucleotide. In the absence of an integrated insertion polynucleotide, a blocker polynucleotide hybridizes to both the first target sequence and the second target sequence of the target polynucleotide sequence. In some embodiments, the blocker polynucleotide is not extendable by a polymerase.

As used herein, the terms "nucleic acid" and "polynucleotide" and are not limited by length and are generic to linear polymers of polydeoxyribonucleotides (containing 2-deoxy-D-ribose), polyribonucleotides (containing D-ribose), and any other N-glycoside of a purine or pyrimidine base, or modified purine or pyrimidine bases. These terms include double- and single-stranded DNA, as well as double- and single-stranded RNA.

A nucleic acid sequence or polynucleotide can comprise phosphodiester linkages or modified linkages including, but not limited to phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages.

A nucleic acid sequence or polynucleotide can comprise the five biologically occurring bases (adenine, guanine, thymine, cytosine and uracil) and/or bases other than the five biologically occurring bases. These bases may serve a number of purposes, e.g., to stabilize or destabilize hybridization; to promote or inhibit probe degradation; or as attachment points for detectable moieties or quencher moieties. For example, a polynucleotide of the invention can contain one or more modified, non-standard, or derivatized base moieties, including, but not limited to, $N^6$-methyl-adenine, $N^6$-tert-butyl-benzyl-adenine, imidazole, substituted imidazoles, 5-fluorouracil, 5-bromouracil, 5-chlorouracil, 5-iodouracil, hypoxanthine, xanthine, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil (i.e., thymine), uracil-5-oxyacetic acidmethylester, 3-(3-amino-3-N-2-carboxypropyl) uracil, (acp3)w, 2,6-diaminopurine, and 5-propynyl pyrimidine. Other examples of modified, non-standard, or derivatized base moieties may be found in U.S. Pat. Nos. 6,001,611; 5,955,589; 5,844,106; 5,789,562; 5,750,343; 5,728,525; and 5,679,785, each of which is incorporated herein by reference in its entirety.

Furthermore, a nucleic acid sequence or polynucleotide can comprise one or more modified sugar moieties including, but not limited to, arabinose, 2-fluoroarabinose, xylulose, and a hexose.

"Hybridization melting temperature" or "Tm" refers to the temperature under specified conditions at which a polynucleotide duplex is 50% in single-stranded form and 50% in double-stranded form. Hybridization melting temperature is calculated using the nearest-neighbor two-state model, which is applicable to short DNA duplexes, $$Tm(°C.)=(\Delta H°/(\Delta S°+R\ln[oligo]))-273.15$$

where $\Delta H°$ (enthalpy) and $\Delta S°$ (entropy) are the melting parameters calculated from the sequence and the published nearest neighbor thermodynamic parameter, R is the ideal gas constant (1.987 cal $K^{-1}$ $mole^{-1}$), [oligo] is the molar concentration of a polynucleotide, and the constant of −273.15 converts temperature from Kelvin to degrees Celsius. Nearest neighbor parameters for DNA/DNA base pairs are obtained from Allawi, et al., *Biochemistry* (1997) 36:10581; Allawi, et al., *Biochemistry* (1998) 37:2170; Allawi, et al., *Biochemishy* (1998) 37:9435; and Peyret, et al., *Biochemishy* (1999) 38:3468. Tm depends on monovalent salt concentration ([$Na^+$]) of the solvent. The default concentration of [$Na^+$] is 50 mM. Software programs for calculating Tm are readily available, for example, from Integrated DNA Technologies, Coralville, Iowa.

DETAILED DESCRIPTION OF THE INVENTION

The present invention provides methods, compositions and kits for determining the presence or absence of an integrated insertion polynucleotide. The invention allows for amplifying a nucleic acid sequence adjacent to an integrated insertion polynucleotide therefore providing a positive detection signal when the integrated insertion polynucleotide is present and a negative detection signal when the integrated insertion polynucleotide is absent.

Figure 2:
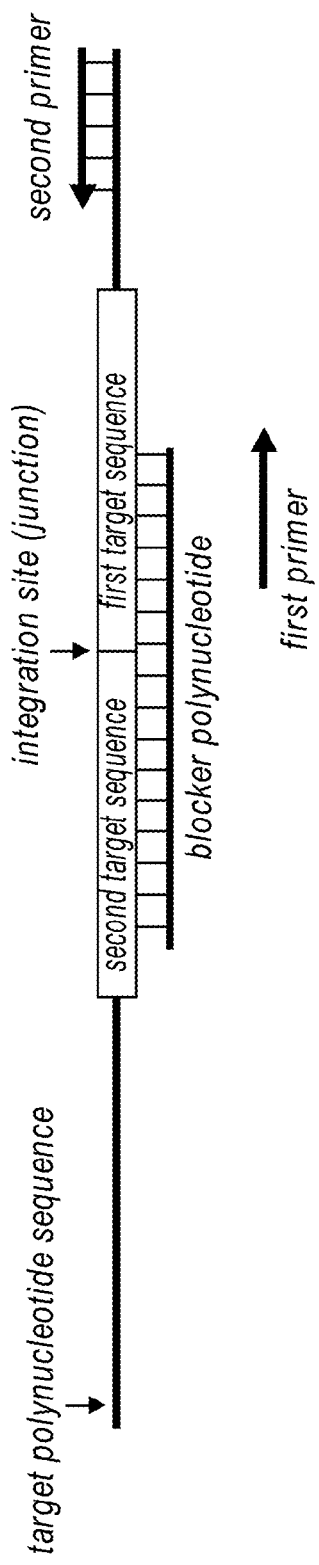
FIG. 2. A schematic showing the relationship between the hybridization sites of the first primer, second primer, blocker polynucleotide, junction and insertion polynucleotide when the insertion sequence is absent and when it is present. The blocker polynucleotide can contain one or more internal mismatches with the target sequence.
Figure 2:
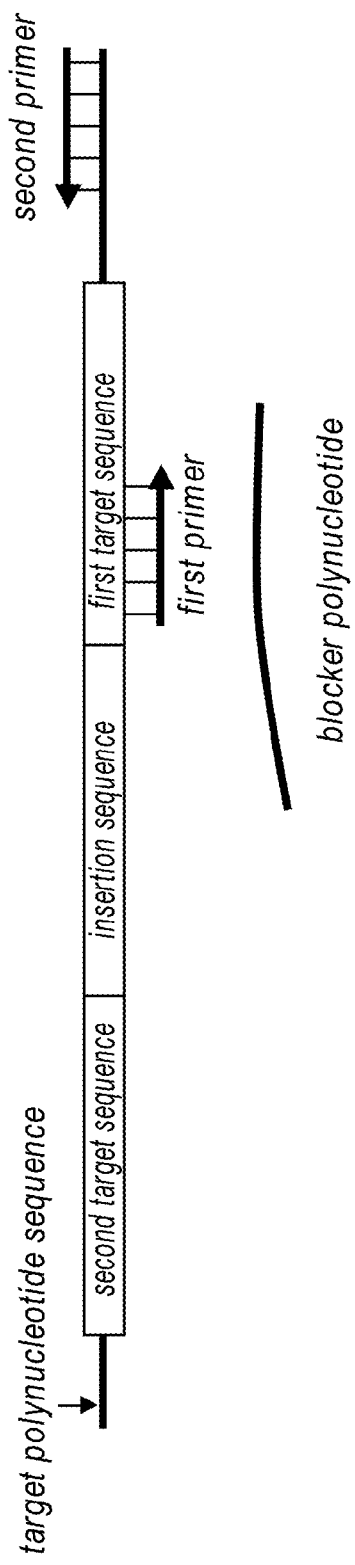

The methods are directed to determining the presence of an integrated insertion polynucleotide in a target polynucleotide sequence by amplifying a polynucleotide sequence adjacent to the integration site (i.e., junction). A positive amplification signal from primers indicating the presence of an integrated insertion polynucleotide is accomplished by employing a blocker polynucleotide that hybridizes to a target polynucleotide sequence spanning the junction in the absence of an integrated insertion polynucleotide. See, FIG. 2. Preferably, the blocker can not be extended by a polymerase.

The blocker polynucleotide competes for hybridization to the target polynucleotide sequence with the first primer (i.e., "the competing primer," either forward or reverse) used to amplify the polynucleotide sequence adjacent to the integration site. In the absence of an integrated insertion polynucleotide, the blocker polynucleotide has a hybridization melting temperature that is relatively higher than the hybridization melting temperature of the first (i.e., competitive) primer. Therefore, in the absence of an integrated insertion polynucleotide, the blocker polynucleotide anneals to the target polynucleotide sequence and no polynucleotide sequence is amplified, indicating the absence of an integrated insertion polynucleotide. In the presence of an integrated insertion polynucleotide, the blocker polynucleotide has a hybridization melting temperature that is relatively lower than the hybridization melting temperature of the first (i.e., competitive) primer. Therefore, in the presence of an integrated insertion polynucleotide, the first (i.e., competing) primer anneals to the target polynucleotide sequence, and an amplicon is amplified from the first (i.e., competitive) primer and the second (i.e., non-competitive) primer, indicating the presence of an integrated insertion polynucleotide. See, FIG. 2.

Figure 1:
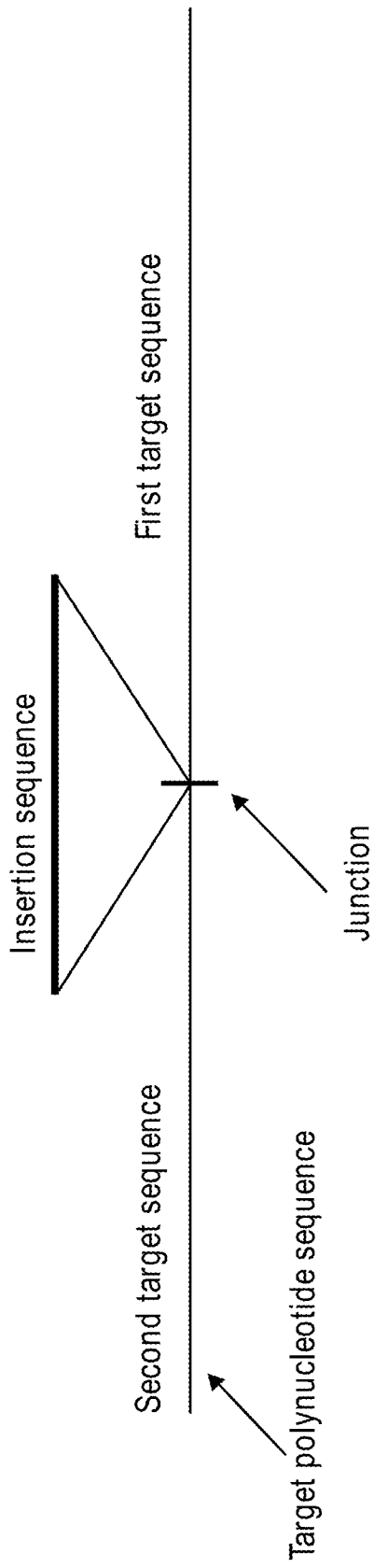
FIG. 1. A schematic showing the relationship between the first target sequence, the second target sequence, the junction and the insertion polynucleotide. The first and second target sequences can be from a non-coding sequence, the same or different reading frames or gene sequence.

In some embodiments, the first primer and the blocker polynucleotide compete for hybridization to a subsequence within the target polynucleotide sequence that is on the same side of the junction as the hybridization site of the second primer. Referring to FIG. 1, in this embodiment, the first primer and the blocker polynucleotide compete for hybridization to a sequence within the first target sequence. The second primer also hybridizes to the first target sequence. In the presence of an integrated insertion polynucleotide, the amplicon does not include the sequence of the integrated insertion polynucleotide.

In some embodiments, the first primer and the blocker polynucleotide compete for hybridization to a subsequence within the target polynucleotide sequence that is on the opposite side of the junction from the hybridization site of the second primer. Referring to FIG. 1, in this embodiment, the first primer and the blocker polynucleotide compete for hybridization to a sequence within the second target sequence while the second primer hybridizes to the first target sequence. In the presence of an integrated insertion polynucleotide, the amplicon includes the sequence of the integrated insertion polynucleotide. In this embodiment, the insertion polynucleotide sequence is a length that can be practicably amplified, for example, less than about 2 kb.

Optionally, the relative hybridization Tm of the blocker polynucleotide and the first primer can be reversed such that amplification occurs when the integrated insertion polynucleotide is absent. In this case, the first primer and the blocker polynucleotide hybridize to a common sequence in the first target sequence proximal to the junction, wherein the blocker has a higher Tm for hybridizing to the common sequence than the first primer when the insertion polynucleotide is integrated into the junction and the blocker polynucleotide has a lower Tm for hybridizing to the common sequence than the first primer when the integrated insertion polynucleotide is not present in the junction, thereby allowing for amplification when the integrated insertion is absent.

Methods

The methods find use in determining the presence or absence in a target polynucleotide sequence of an integrated insertion polynucleotide, including without limitation a mobile genetic element, a transposon, a translocational fusion sequence (e.g., an oncogene, a tumor marker fusion sequence, a transgene insertion site, including a CRE/LOX site), or a retroviral genomic sequence.

Target Polynucleotide Sequence

The target polynucleotide sequence comprises a junction of a first target sequence and a second target sequence, and optionally an insertion polynucleotide (see, FIG. 1). In some embodiments, the insertion polynucleotide is from the same genome as the target polynucleotide sequence (e.g., a transposon, a translocational fusion sequence). In some embodiments, the methods are used to determine the presence or absence of a tumor marker translocation fusion sequence, for example, c-erb-B2 RNA splice variants; bcr/abl fusion; and translocations affecting Bcl-2 or Bcl-10.

In some embodiments, the insertion polynucleotide is from a genome different from the target polynucleotide sequence (e.g., a mobile genetic element, a retroviral genomic sequence). The different genome can be from the same or a different organism. In some embodiments, the methods are used to determine the presence or absence of a mobile genetic element integrated into a bacterial host genome that conveys antibiotic resistance.

In some embodiments, the methods can be carried out for identifying the presence or absence of an insertion polynucleotide integrated into a target host genome. The host genome can be from any source. The genomic DNA can be prokaryotic or eukaryotic. It can be from bacteria, fungi, plants or animals. The host genomic DNA can be from a pathogen to a plant or animal host, for example, viral, bacterial, fungal or parasitic. Genomic DNA can be, for example, from bacterial genera pathogenic to an animal host and capable of developing resistance to antimicrobial agents, including *Staphylococcus, Streptococcus, Escherichia coli, Mycobacterium, Bacillus, Enterococcus, Enterobacter, Haemophilus, Pseudomonas, Klebsiella, Acinetobacter, Listeria, Helicobacter, Salmonella, Neisseria, Legionella*, etc. In some embodiments, the host genomic DNA is from a *Staphylococcus* species, for example, *Staphylococcus aureus, Staphylococcus haemolyticus, Staphylococcus saprophyticus, Staphylococcus epidermidis, Staphylococcus xylosus, Staphylococcus warneri, Staphylococcus vitulinus, Staphylococcus sussinus, Staphylococcus simulans, Staphylococcus sciuri*, etc.

The host genomic DNA can be from an animal host. The animal can be human or non-human, and is can be mammalian, including domestic animals and agricultural animals. Domestic animals include canine, feline, rodent, lagomorpha, hamster, chinchilla, mutts, murine. Agricultural animals include equine, bovine, ovine, porcine and chickens. The genomic DNA can be tested from cells or tissues, as appropriate.

The host genomic DNA can be purified and/or isolated according to techniques well known in the art, for example, those described in Sambrook and Russell, *Molecular Cloning: A Lahoralory Manual,* 3rd Edition, 2001, Cold Spring Harbor Laboratory Press and Ausubel, et al, *Current Protocols in Molecular Biology,* 1987-2007, John Wiley & Sons.

Insertion Polynucleotide

The insertion polynucleotide can be any nucleic acid sequence that can be inserted between two linked polynucleotide sequences. The insertion polynucleotide can, but need not, convey an identifiable phenotypic trait in the host when integrated into the target polynucleotide sequence. For example, as described above, the insertion polynucleotide can be a retroviral genome sequence, a transposon, a translocational fusion sequence or a mobile genetic element.

In some embodiments, the insertion polynucleotide is a mobile genetic element that imparts resistance to antimicrobial agents. Mobile genetic elements that convey resistance to antibiotics in bacteria having them integrated into their genomic DNA include those that encode sequences that neutralize the antibacterial mechanism of beta-lactam and aminoglycoside antibiotics.

For example, a mobile genetic element that encodes a penicillin binding protein can impart bacterial resistance to beta lactam antibiotics. Exemplified beta lactam antibiotics include methicillin, penicillins (e.g., penicillin G, penicillin V), amoxicillin, ampicillin, oxacillin, cloxacillin, dicloxacillin, nafcillin, carbenicillin, ticarcillin, mezlocillin, azlocillin, piperacillin, and the like. Beta lactam antibiotics are described, for example, in Chapter 45 of *Goodman and Gilman's Pharmacological Basis of Therapeutics,* eds., Hardman and Limbird, 2001, McGraw-Hill. One example of a mobile genetic element that conveys resistance to beta lactam antibiotics is the mecA complex, which encodes a penicillin binding protein and imparts resistance to methicillin, penicillins and other beta lactam antibiotics in bacteria when it is integrated into the bacterial host genome. Exemplified GenBank accession numbers for penicillin binding protein polypeptide sequences include YP_252006; CAH17594, AAY60807; BAB07108; CAC95693; AAK39559; NP_716793; and AAU27457. Exemplified GenBank accession numbers for nucleotide sequences encoding penicillin binding protein polypeptides include NC_007168 (GeneID 3482097); AY894415; AP006716; AM048803; Y13096; EFY17797; EFA290435; and AE17323. Penicillin binding proteins can be characterized by several common protein structural motifs, including MecA_N (pfam05223), PBP_dimer (pfam03717), and Transpeptidase (pfam00905).

A mobile genetic element that encodes an aminoglycoside phosphotransferase or an aminoglycoside acetyltransferase can impart bacterial resistance to aminoglycoside antibiotics. Exemplified aminoglycoside antibiotics include gentamicin, tobramycin, amikacin, netilmicin, kanamycin, streptomycin and neomycin. Aminoglycoside antibiotics are described, for example, in Chapter 46 of *Goodman and Gilman's,* supra. Exemplified GenBank accession numbers for aminoglycoside phospho- or acetyl-transferase polypeptide sequences include YP_253526; NP_115315; CAD60196; AAC53691; AAX82584; AAK63041; AAT61777; AAG13458; AAK63040; and CAH19071. Exemplified GenBank accession numbers for nucleotide sequences encoding aminoglycoside phospho- or acetyl-transferase polypeptides include NC_007168 (GeneID 3482424). Aminoglycoside phospho- or acetyl-transferases can be characterized by common protein structural motifs, including APH (phosphotransferase enzyme family, pfam01636) and Acetyltransf_1 (acetyltransferase (GNAT) family, pfam00583).

An insertion polynucleotide is at least about 10 nucleotide bases in length, for example, about 10, 20, 50, 100, 500, 1000, 1500, 2000 nucleotides bases in length, or longer.

Integration Sites

A target polynucleotide sequence susceptible to integration of an insertion polynucleotide will have one or more integration sites. The integration site can be determined by the target polynucleotide sequence or by the nature of the insertion polynucleotide. The methods are generally suited to detecting insertion sequences integrated at recognition sites of site-specific recombinases (e.g., Cre, Flp or PhiC31 integrase), including without limitation loxP (e.g., loxP2, loxP3, loxP23, loxP511, loxB, loxC2, loxL, loxR), frt, dif, flp, and att target integration sequences. These are known in the art (see, for example, Sorrell and Kolb, *Biotechnol. Adv.* (2005) 23:431; see also, Fluit and Schmitz, *Clin Microbiol Infect* (2004) 10:272).

In *Staphylococcus,* a site for integration (i.e., junction site) of the SCCmec complex carrying the mecA gene is the attB site within the orfX open reading frame. Exemplified *Staphylococcus* orfX open reading frame sequences include GenBank accession numbers NC_007168 (GeneID 3482010); NC_002758 (GeneID 1119986); and NC_007350 (GeneID 3615252).

Primers

The primers of the invention are capable of acting as a point of initiation of DNA synthesis under conditions allowing for amplification, in which synthesis of a primer extension product complementary to a nucleic acid strand is induced, i.e., in the presence of four different nucleoside triphosphates and an agent for extension (e.g., a DNA polymerase or reverse transcriptase) in an appropriate buffer and at a suitable temperature (see, for example, *Molecular Diagnostic PCR Handbook,* Viljoen, et al., eds., 2005 Kluwer Academic Pub.; *PCR Protocols,* Bartlett, et al., eds., 2003, Humana Press; and *PCR Primer: A Laboratory Manual,* Dieffenbach, et al., eds., 2003, Cold Spring Harbor Laboratory Press). A primer is preferably a single-stranded DNA. The appropriate length of a primer depends on, for example, the intended hybridization melting temperature (Tm) and location of the primer but typically ranges from 10 to 50 nucleotides, preferably from 15-35 or 18-22 nucleotides. Short primer molecules generally require lower temperatures to form sufficiently stable hybrid complexes with the template. A primer need not reflect the exact sequence of the template nucleic acid, but must be sufficiently complementary to hybridize with the template. In some embodiments, the primers of the invention can have no mismatches, the same number of mismatches (e.g., 0, 1, 2, 3, 4, 5, etc.), or fewer hybridization mismatches in comparison to the blocker polynucleotide. The primers of the invention can also have no hybridization mismatches. The design of suitable primers for the amplification of a given target sequence is well known in the art and described in, for example, the literature cited herein.

The first (forward or reverse) primers of the invention compete with the blocker polynucleotide for hybridization to a common sequence within the target polynucleotide sequence (e.g., competitive displacement based on relative Tm). The first primers are designed to have a relatively lower hybridization melting temperature in comparison to the hybridization melting temperature of the blocker polynucleotide when no insertion nucleotide is present. The first primers further are designed to have a relatively higher hybridization melting temperature in comparison to the hybridization melting temperature of the blocker polynucleotide when an insertion polynucleotide is present.

In some embodiments, the hybridization melting temperature of the first (i.e., competitive) primer will be between about 5° C.-15° C. higher or lower in comparison to the blocker polynucleotide, as appropriate. In some embodiments, the hybridization melting temperature of the first primer is about 5° C., 6° C., 7° C., 8° C., 9° C., 10° C., 11° C., 12° C., 13° C., 14° C. or 15° C. higher or lower in comparison to the blocker polynucleotide, as appropriate. In some embodiments, the difference in hybridization melting temperature can be more or less than this exemplified range.

The first and second primers of the invention can have a hybridization melting temperature ranging from about 50° C. to about 65° C., between about 55° C. to about 60° C., for example. In some embodiments, hybridization melting temperature of a primer is about 50° C., 51° C., 52° C., 53° C., 54° C., 55° C., 56° C., 57° C., 58° C., 59° C., 60° C., 61° C., 62° C., 63° C., 64° C. or 65° C. However, the hybridization melting temperature of the first and second primers can be higher or lower than this temperature range.

Methods of designing a polynucleotide to have a desired hybridization melting temperature apply to both primers and blockers, and are known in the art. Hybridization melting temperature can be adjusted, for example, by the number of guanosine (G) or cytidine (C) nucleosides, by adjusting the length of the polynucleotide, or by incorporating one or more bases that are mismatched with the target polynucleotide sequence. Generally, polynucleotides with greater numbers of G or C nucleosides, of longer length, or with greater numbers of matching nucleosides will have higher hybridization melting temperatures. In some embodiments, the hybridization melting temperature differences between the first primer and the blocker are adjusted by introducing a greater number of bases mismatched with the target polynucleotide into the blocker sequence in comparison to the first primer sequence. For example, in some embodiments, the first primer has no bases mismatched with the target polynucleotide sequence and the blocker has one or more bases mismatched with the target polynucleotide sequence.

In some embodiments, the blocker polynucleotide and the first primer hybridize to a common sequence in the first target sequence proximal or adjacent to the junction that includes the full length of first primer. In some embodiments, the blocker polynucleotide and the first primer hybridize to a common sequence adjacent to the junction that is complementary to a portion of the first primer, for example 50%, 60%, 70%, 80% or 90% of the 5'-end or 3'-end the of the first primer. The common sequence competitively hybridized by blocker polynucleotide and the first primer can be from 10-30 bases in length, for example, 12-25 or 15-20 bases in length, for example, 10, 11, 12, 13, 14, 15, 16, 17, 18, 19, 20, 21, 22, 23, 24, 25, 26, 27, 28, 29 or 30 bases in length, or longer or shorter.

The first primers are designed to anneal to a nucleic acid sequence within the target polynucleotide sequence that is proximal or adjacent to the integration site for the insertion polynucleotide. In the embodiments where the first primer and the blocker polynucleotide compete to hybridize to a common sequence in the first target sequence, the 5'-end of the first primer can anneal within, e.g., about 30, 25 or 20 nucleotide base positions of the integration site, for example, within about 15, 10 or 5 nucleotide base positions of the integration site, or sometimes abuts the integration site. In the embodiments where the first primer and the blocker polynucleotide compete to hybridize to a common sequence in the second target sequence, the 5'-end of the first primer can anneal within, e.g., about 40, 35 or 30 nucleotide base positions of the integration site, for example, within about 25, 20 or 15 nucleotide base positions of the integration site. The second primer anneals to a nucleic acid sequence in the target polynucleotide sequence such that the amplicon amplified from the first and second primer can be reliably detected. In some embodiments, the amplicon will be about 100, 200, 300, 400, 500, 600, 800, 1000, 1500, 2000 nucleic acid bases in length, or any integer of nucleic acid bases in length from about 100-2000, but can be shorter or longer, as appropriate.

In some embodiments, the first and second primers anneal to an orfX gene sequence in a *Staphylococcus* target polynucleotide sequence. In some embodiments, the first primer is a reverse primer comprising the sequence selected from the group consisting of 5'-CTTATGATACGCTTCTCCTCGC-3' (SEQ ID NO:2); 5'-GCTTCTCCACGCATAATCTTAAAT-GCTCT-3' (SEQ ID NO:9); and 5'-TACTTATGATACGCT-TCTCC-3' (SEQ ID NO:10). In some embodiments, the second primer is a forward primer comprising the sequence 5'-AGGGCAAAGCGACTTTGTATTC-3' (SEQ ID NO: 1).

The primers can incorporate additional features which allow for the detection or immobilization of the primer but do not alter the basic property of the primer, i.e., that of acting as a point of initiation of DNA synthesis. For example, primers may contain an additional nucleic acid sequence at the 5' end which does not hybridize to the target polynucleotide, but which facilitates cloning of the amplified product. The region of the primer which is sufficiently complementary to the template to hybridize is referred to herein as the hybridizing region. In some embodiments, the first primer and/or the second primer comprise about 1-10 consecutive cytosine or guanosine bases (SEQ ID NO:11) at their 5'-end, for example, 1, 2, 3, 4, 5, 6, 7, 8, 9 or 10 consecutive cytosine or guanosine bases preceding the hybridizing region at the 5'-end.

The first and second primers can also be modified and include at least one nucleotide containing a sugar other than the conventional 2'-deoxy-D-ribose or D-ribose found in naturally occurring DNA and RNA. Similarly, as used herein, a "modified polynucleotide" refers to a polynucleotide containing a sugar other than the conventional 2'-deoxy-D-ribose or D-ribose found in naturally occurring DNA and RNA, and encompasses nucleotides in which the sugar is modified by the addition or substitution of a side group, or in which the sugar is a stereoisomer of the conventional 2'-deoxy-D-ribose or D-ribose found in naturally occurring DNA and RNA, or both. The terms are not used to indicate that a modified primer or nucleotide is the product of a process of modification, but rather to indicate the presence of differences in the polynucleotide backbone relative to naturally occurring DNA or RNA. In particular, the primers of the present invention can be synthesized to contain a modified nucleotide, although the chemical modification of a primer initially containing only conventional nucleotides can provide an alternative synthesis.

Blocker Polynucleotide

The blocking or blocker polynucleotides ("blockers") of the invention do not operate as a point of extension under amplification or extension conditions where the first and second primers operate as a point of extension. In some embodiments, this is because they have a blocking moiety attached to their 3'-end or because they lack a nucleophilic moiety attached to their 3'-end (e.g., a hydroxyl moiety). A blocker polynucleotide is preferably a single-stranded DNA. The appropriate length of a blocker polynucleotide depends on, for example, the intended hybridization melting temperature (Tm) and location of the blocker but typically ranges from 25 to 60 nucleotides, preferably from about 30-50 or 35-45 nucleotides, or any integer of nucleotide bases within these ranges. Shorter blocker polynucleotides generally require lower temperatures to form sufficiently stable hybrid complexes with the template. A blocker polynucleotide need not reflect the exact sequence of the template nucleic acid, but must be sufficiently complementary to hybridize with the template. A blocker polynucleotide can hybridize to a longer or shorter sequence segment of the first target sequence relative to the first primer. A blocker polynucleotide can be longer or shorter than a first primer.

The Tm of the blocker polynucleotide can be varied by adjusting one or more of several parameters, including for example, its length, the location and complementary sequence of the target polynucleotide to which it hybridizes (i.e., hybridization condition), and the number of internal mismatches. The blocker polynucleotides of the invention can have zero, one, two, three, four or more internal nucleotide bases mismatched with the target polynucleotide sequence, for example. The mismatched bases preferably are localized to the region of the blocker that anneals to the first or second target sequence, i.e., the subsequence in the target polynucleotide sequence in which the first primer and the blocker compete for hybridization. The design of polynucleotide sequences to hybridize to a target nucleotide sequence is well known in the art and described in, for example, the literature cited herein.

The blocker polynucleotide competes with the first primer of the invention for hybridization to a common sequence within the first or second target subsequence within target polynucleotide sequence. See, FIGS. 1 and 2. The common target sequence competitively hybridized by the blocker polynucleotide and the first primer can be complementary to the full-length of the first primer or a portion of the first primer. The blocker polynucleotides are designed to have a relatively higher hybridization melting temperature in comparison to the hybridization melting temperature of the first primer when no insertion nucleotide is present. The blocker polynucleotides are further designed to have a relatively lower hybridization melting temperature in comparison to the hybridization melting temperature of the first primer when an insertion polynucleotide is present. In some embodiments, the hybridization melting temperature of the blocker polynucleotide will be between about 5° C.-15° C. higher or lower in comparison to the first primer, as appropriate. In some embodiments, the hybridization melting temperature of the blocker polynucleotide is about 5° C., 6° C., 7° C., 8° C., 9° C., 10° C., 11° C., 12° C., 13° C., 14° C. or 15° C. higher or lower in comparison to the first primer, as appropriate. In some embodiments, the difference in hybridization melting temperature can be more or less than this exemplified range.

For example, the blocker polynucleotides of the invention can have a hybridization melting temperature ranging from about 60° C. to about 75° C., for example, between about 65° C. to about 70° C., when no insertion nucleotide is present. In some embodiments, hybridization melting temperature of the blocker polynucleotides when no insertion nucleotide is present is about 60° C., 61° C., 62° C., 63° C., 64° C., 65° C., 66° C., 67° C., 68° C., 69° C., 70° C., 71° C., 72° C., 73° C., 74° C. or 75° C. The blocker polynucleotides can have a hybridization melting temperature ranging from about 40° C. to about 55° C., for example, between about 45° C. to about 50° C., when an insertion nucleotide is present. In some embodiments, hybridization melting temperature of the blocker polynucleotides when an insertion nucleotide is present is about 40° C., 41° C., 42° C., 43° C., 44° C., 45° C., 46° C., 47° C., 48° C., 49° C., 50° C., 51° C., 52° C., 53° C., 54° C. or 55° C.

The blocker polynucleotides are designed to anneal to a nucleic acid sequence within the target polynucleotide sequence that overlaps the integration site for the insertion polynucleotide. The blocker polynucleotides can anneal about 30, 25, 20, 15 or 10 nucleotide base positions spanning across the integration site or junction site.

In some embodiments, the blocker polynucleotide anneals to an orfX gene sequence in a *Staphylococcus* host genome, straddling an attB integration site. In some embodiments, the blocker polynucleotide comprises one or more polynucleotide sequences selected from the group consisting of: 5'-CAGAATTTTTTAGTTTTACTTATGATACGC-CTCTCCTCGC-3' (SEQ ID NO:3); 5'-TAAAAAACTCCTCCGCTACTTAT-GATACGCTTCTCCTCGC-3' (SEQ ID NO:4); 5'-CTCCT-CATACAGAATTTTTTAGTTTTACTTATGATACGC CTCTCCTCGC-3' (SEQ ID NO:6); 5'-CTCCTCATACA-GAATTTTTTAGTTTTACT TATGATACGCCTCTC-CACGCATAATC-3' (SEQ ID NO:7): and 5'-CTCCTCATAC AGAATTTTTTAGTTTTACTTAT-GATACGCCTCTCCACGCATAATCTTAAATGC-3' (SEQ ID NO:8).

Exemplified pairs of blocker polynucleotides and first primers (here, reverse primers) that hybridize to a common nucleic acid sequence include those listed in Table 1, below.

TABLE 1

Blocker-GCG49 (SEQ ID NO: 6)
CTCCTCATACAGAATTTTTTAGTTTTACTTATGATACGCCTCTCCTCGC

Reverse Primer (SEQ ID NO: 9)
GCTTCTCCACGCATAATCTTAAATGCTCT

Blocker-CTA55 (SEQ ID NO: 7)
CTCCTCATACAGAATTTTTTAGTTTTACTTATGATACGCCTCTCCACGC

ATAATC

Reverse Primer (SEQ ID NO: 9)
GCTTCTCCACGCATAATCTTAAATGCTCT

Blocker-CGT63 (SEQ ID NO: 8)
CTCCTCATACAGAATTTTTTAGTTTTACTTATGATACGCCTCTCCACGC

ATAATCTTAAATGC

Reverse Primer (SEQ ID NO: 9)
GCTTCTCCACGCATAATCTTAAATGCTCT

The blocker polynucleotides preferably comprise a blocking moiety at their 3'-end, that prevents their extension. Exemplified blocking moieties include replacing the 3'-terminal hydroxyl group with a hydrogen, an amino or a phosphate group. In some embodiments, the blocking moiety on the blocker polynucleotide is a phosphate or hexylamine.

Modified Polynucleotides

Both primers and blocker polynucleotides will generally contain phosphodiester bonds, although in some cases, as outlined herein, nucleic acid analogs can be used that may have alternate backbones, including, for example and without limitation, phosphoramide (Beaucage et al. (1993) *Tetrahedron* 49(10):1925 and references therein; Letsinger (1970) *J. Org. Chem.* 35:3800; Sprinzl et al. (1977) *Eur. J. Biochem.* 81:579; Letsinger et al. (1986) *Nucl. Acids Res.* 14: 3487; Sawai et al. (1984) Chem. Lett. 805; Letsinger et al. (1988) *J.*

*Am. Chem. Soc.* 110:4470; and Pauwels et al. (1986) *Chemica Scripta* 26: 1419, which are each incorporated by reference), phosphorothioate (Mag et al. (1991) *Nucleic Acids Res.* 19:1437; and U.S. Pat. No. 5,644,048, which are both incorporated by reference), phosphorodithioate (Brio et al. (1989) *J. Am. Chem. Soc.* 111:2321, which is incorporated by reference), O-methylphosphoroamidite linkages (see Eckstein, *Oligonucleotides and Analogues: A Practical Approach*, Oxford University Press (1992), which is incorporated by reference); and peptide nucleic acid (PNA) backbones and locked nucleic acid backbones (LNA) and linkages (see, Egholm (1992) *J. Am. Chem. Soc.* 114:1895; Meier et al. (1992) *Chem. Int.* Ed. Engl. 31:1008; Nielsen (1993) *Nature* 365:566; and Carlsson et al. (1996) *Nature* 380:207, Demidov, *Trends Biotechnol* (2003) 21:4-7; and Vester and Wengel, *Biochemistry* (2004) 43:132:33-41, which are each incorporated by reference).

Other analog nucleic acids include those with positively charged backbones (Denpcy et al. (1995) Proc. Natl. Acad. Sci. USA 92:6097, which is incorporated by reference); non-ionic backbones (U.S. Pat. Nos. 5,386,023, 5,637,684, 5,602, 240, 5,216,141 and 4,469,863; Angew (1991) *Chem. Intl.* Ed. English 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, Ed. Y. S. Sanghvi and P. Dan Cook; Mesmaeker et al. (1994) *Bioorganic & Medicinal Chem. Lett.* 4: 395; Jeffs et al. (1994) *J. Biomolecular NMR* 34:17; and *Tetrahedron Lett.* 37:743 (1996), which are each incorporated by reference) and non-ribose backbones, including those described in U.S. Pat. Nos. 5,235,033 and 5,034,506, and Chapters 6 and 7, ASC Symposium Series 580, Ed. Y. S. Sanghvi and P. Dan Cook, which references are each incorporated by reference. Nucleic acids containing one or more carbocyclic sugars are also included within the definition of nucleic acids (see Jenkins et al. (1995) *Chem. Soc. Rev.* pp 169-176, which is incorporated by reference). Several nucleic acid analogs are also described in, e.g., Rawls, *C & E News* Jun. 2, 1997 page 35, which is incorporated by reference. These modifications of the ribose-phosphate backbone can be used to facilitate the addition of additional moieties such as labels, or to alter the stability and half-life of such molecules in physiological environments.

In addition to the naturally occurring heterocyclic bases that are typically found in nucleic acids (e.g., adenine, guanine, thymine, cytosine, and uracil), nucleic acid analogs also include those having non-naturally occurring heterocyclic or modified bases, many of which are described, or otherwise referred to, herein. In particular, many non-naturally occurring bases are described further in, e.g., Seela et al. (1991) *Helv. Chico. Acta* 74:1790, Grein et al. (1994) *Bioorg. Med. Chem. Lett.* 4:971-976, and Seela et al. (1999) *Helv. Chim. Acta* 82:1640, which are each incorporated by reference. To further illustrate, certain bases used in nucleotides that act as melting temperature (Tm) modifiers are optionally included. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, which is incorporated by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like. Examples of modified bases and nucleotides are also described in, e.g., U.S. Pat. Nos. 5,484,908, 5,645,985, 5,830,653, 6,639,059, 6,303,315 and U.S. Pat. Application Pub. No. 2003/0092905, which are each incorporated by reference.

Amplification Reactions

Amplification of an RNA or DNA template using reactions is well known (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of target DNA sequences directly from mRNA, from cDNA, from genomic libraries or cDNA libraries. The reaction is preferably carried out in a thermal cycler to facilitate incubation times at desired temperatures. See, e.g., PCR PRIMER, A LABORATORY MANUAL (Dieffenbach, ed. 2003) Cold Spring Harbor Press.

Exemplary PCR reaction conditions allowing for amplification of an amplicon typically comprise either two or three step cycles. Two step cycles have a denaturation step followed by a hybridization/elongation step. Three step cycles comprise a denaturation step followed by a hybridization step followed by a separate elongation step.

In some embodiments, an amplified amplicon in the presence of an insertion polynucleotide integrated into the target polynucleotide is detected by real-time PCR. Real-time RT-PCR is a method that utilizes specifically engineered DNA sequences (two primers and a fluorescently labeled probe) to detect and quantify target sequences of DNA. The probe contains a fluorescent reporter dye on one end and a quencher dye on the other. During each amplification cycle, the probe first attaches to the target sequence of DNA, followed by attachment of the primers. As the DNA strand is copied, the reporter dye is released from the probe and emits a fluorescent signal. The amount of fluorescence increases with each cycle of PCR in proportion to the amount of target DNA. This results in direct detection and quantification of the target DNA sequence with a high degree of specificity, accuracy, and sensitivity.

In some embodiments, the multiple amplification reactions are performed by multiplex PCR. Multiplex PCR reactions refer to a PCR reaction where more than one primer set is included in the reaction pool allowing 2 or more different DNA targets to be amplified by PCR in a single reaction tube. Multiplex PCR can be quantitative and can be evaluated "real-time." Multiplex PCR reactions are useful for validation, diagnostic and prognostic purposes. Multiplex PCR reactions can be carried out using manual or automatic thermal cycling. Any commercially available thermal cycler may be used, such as, e.g., Perkin-Elmer 9600 cycler. Using multiplex PCR, at least 5, 6, 7, 8, 9, 10, 15, 20, 25, 30, 50, 100 or more target polynucleotides can be evaluated for the presence or absence of an integrated insertion polynucleotide.

Isothermic amplification reactions are also known and can be used according to the methods of the invention. Examples of isothermic amplification reactions include strand displacement amplification (SDA) (Walker, et al. *Nucleic Acids Res.* 20(7): 1691-6 (1992); Walker *PCR Methods Appl* 3(1):1-6 (1993)), transcription-mediated amplification (Phyffer, et al., *J. Clin. Microbiol.* 34:834-841 (1996); Vuorinen, et al., *J. Clin. Microbiol.* 33:1856-1859 (1995)), nucleic acid sequence-based amplification (NASBA) (Compton, *Nature* 350(6313):91-2 (1991), rolling circle amplification (RCA) (Lisby, *Mol. Biotechnol.* 12(1):75-99 (1999)); Hatch et al., *Genet. Anal.* 15(2):35-40 (1999)) and branched DNA signal amplification (bDNA) (see, e.g., Iqbal et al., *Mol. Cell Probes* 13(4):315-320 (1999)). Other amplification methods known to those of skill in the art include CPR (Cycling Probe Reaction), SSR (Self-Sustained Sequence Replication), SOA (Strand Displacement Amplification), QBR (Q-Beta Replicase), Re-AMP (formerly RAMP), RCR (Repair Chain Reaction), TAS (Transorbtion Based Amplification System), and HCS.

The concentration of the magnesium salt in the reaction mixture can be important when trying to copy different target DNA sequences. Thus, some variation of the concentration of the magnesium salt, e.g., magnesium chloride, may be required to optimize the reaction to amplify the target polynucleotide sequences of interest. One of skill can vary the concentration of magnesium salt or ion present in the reaction mixture to arrive at the proper conditions for amplification.

In some embodiments, a second pair of primers is included in the amplification reaction that allow for the amplification of a control sequence in the target polynucleotide, for example, to quantify the amount of target polynucleotide in an assay.

In some embodiments, the molar ratio of the one or more blocker polynucleotides to the competitive first primer in the amplification reaction can be optimized. In some embodiments, the molar ratio of the one or more blocker polynucleotides to the competitive first primer in the amplification reaction is greater than a 1:1 molar ratio of blocker polynucleotide(s) to first primer, for example, from about 5:1 to about 30:1, for example, about a 5:1, 10:1, 20:1, 25:1 or 30:1 molar ratio of blocker polynucleotide(s) to first primer.

Detection of Amplified Polynucleotides

Amplified nucleic acid sequences ("amplicons") can be detected using any method known in the art. For example, amplicons can be detected in an agarose gel using ethidium bromide. The presence of an insertion polynucleotide is indicated by the presence of an amplicon signal or the increased presence of an amplicon signal in comparison to a control target polynucleotide sequence, for example, a target polynucleotide sequence known not to have an insertion polynucleotide, for example, a methicillin-sensitive *Staphylococcus aureus* (MSSA).

In some embodiments, amplicons are detected using probes that specifically hybridize to the amplicon and are detectable upon hybrizidation to the amplicon. Numerous types of probes are capable of hybridizing to and detecting a particular polynucleotide sequences. In some cases, the probe also comprises a fluorophore or enzyme, as described below, which allows for the detection of the binding of the probe to its complementary target sequence.

Probe concentration should be sufficient to bind to the amount of target or control sequences that are amplified so as to provide an accurate assessment of the quantity of amplified sequence. Those of skill in the art will recognize that the amount of concentration of probe will vary according to the binding affinity of the probe as well as the quantity of sequence to be bound. Typical probe concentrations will range from 0.01 µM to 0.5 µM. Typical probe length will range from about 20-40 nucleotide bases in length, for example, about 25-35 nucleotide bases in length, or any integer number of nucleotide bases within these ranges.

The present invention can employ many different kinds of nucleic acid hybridization probes for detection of amplicon. Typically, for signal generation, the probes utilize a change in the fluorescence of a fluorophore due to a change in its interaction with another molecule or moiety brought about by changing the distance between the fluorophore and the interacting molecule or moiety. Alternatively, amplicons can be detected using other methods, for example, using radioactively-labeled or enzymatically-labeled probes.

In some instances, multiple fluorescent labels are employed. In a preferred embodiment, at least two fluorescent labels are used which are members of a fluorescence resonance energy transfer (FRET) pair. FRET is phenomenon known in the art wherein excitation of one fluorescent dye is transferred to another without emission of a photon. A FRET pair consists of a donor fluorophore and an acceptor fluorophore. The fluorescence emission spectrum of the donor and the fluorescence absorption spectrum of the acceptor usually overlap, and the two molecules must be in close proximity. The distance between donor and acceptor at which 50% of donors are deactivated (transfer energy to the acceptor) is defined by the Forster radius ($R_o$), which is typically 10-100 Å. Changes in the fluorescence emission spectrum comprising FRET pairs can be detected, indicating that they are in close proximity (i.e., within 100 Å of each other). This will typically result from the binding or dissociation of two molecules, one of which is labeled with a FRET donor and the other of which is labeled with a FRET acceptor, wherein such binding brings the FRET pair in close proximity. Binding of such molecules will result in an increased fluorescence emission of the acceptor and/or quenching of the fluorescence emission of the donor.

FRET pairs (donor/acceptor) useful in the invention include, but are not limited to, EDANS/fluorescein, IAEDANS/fluorescein, fluorescein/tetramethylrhodamine, fluorescein/LC Red 640, fluorescein/Cy 5, fluorescein/Cy 5.5 and fluorescein/LC Red 705.

in another aspect of FRET, a fluorescent donor molecule and a nonfluorescent acceptor molecule ("quencher") may be employed. In this application, fluorescent emission of the donor will increase when quencher is displaced from close proximity to the donor and fluorescent emission will decrease when the quencher is brought into close proximity to the donor. Useful quenchers include, but are not limited to, DABCYL, QSY 7 and QSY 33. Useful fluorescent donor/quencher pairs include, but are not limited to EDANS/DABCYL, Texas Red/DABCYL, BODIPY/DABCYL, Lucifer yellow/DABCYL, coumarin/DABCYL and fluorescein/QSY 7 dye.

The skilled artisan will appreciate that FRET and fluorescence quenching allow for monitoring of binding of labeled molecules over time, providing cycle-dependent information regarding the time course of binding reactions.

In some embodiments, the amplified nucleic acid sequence is detected using a probe labeled at its 5'-end with a fluorophore and at its 3'-end with a quencher. In a further embodiment, the fluorophore is fluorescein (FAM) and the quencher is QSY7. Alternatively, fluorophore(s) and/or quencher(s) can be located at an internal site within a probe.

In some embodiments, the detectable probe hybridizes to an amplicon corresponding to a *Staphylococcus* orfX sequence. In a further embodiment, the detectable probe comprises the sequence 5'-CGGCCTGCACAAGGACGTCTTA-CAACGTAG-3' (SEQ ID NO:5).

Another type of nucleic acid hybridization probe assay utilizing a FRET pair is the "TaqMan®" assay described in Gelfand et al. U.S. Pat. No. 5,210,015, and Livak et al. U.S. Pat. No. 5,538,848. The probe is a single-stranded polynucleotide labeled with a FRET pair. In a TaqMan® assay, a DNA polymerase releases single or multiple nucleotides by cleavage of the polynucleotide probe when it is hybridized to a target strand. That release provides a way to separate the quencher label and the fluorophore label of the FRET pair.

Yet another type of nucleic acid hybridization probe assay utilizing FRET pairs is described in Tyagi et al. U.S. Pat. No.

5,925,517, which utilizes labeled polynucleotide probes, which are referred to as "Molecular Beacons." See Tyagi, S, and Kramer, F. R., *Nature Biotechnology* 14: 303-308 (1996). A molecular beacon probe is a polynucleotide whose end regions hybridize with one another to form a hairpin in the absence of target but are separated if the central portion of the probe hybridizes to its target sequence. When the probe hybridizes to a target, that is, when the target-recognition sequence hybridizes to a complementary target sequence, a relatively rigid helix is formed, causing the stem hybrid to unwind and forcing the arms apart.

Non-FRET fluorescent probes can also be used. For example, changes in the absorption spectra of the label pair can be used as a detectable signal as an alternative to change in fluorescence. When change in absorption is utilized, the label pair may include any two chromophores, that is, fluorophores, quenchers and other chromophores. The label pair may even be identical chromophores.

Compositions

The invention further provides compositions, including for example, solutions, reaction mixtures, and reaction vessels comprising the first and second primers, blocker polynucleotides and optionally detection probes, as described above.

In some embodiments, compositions comprise first and second primers, and a blocker polynucleotide that each hybridize to a *Staphylococcus* orfX sequence, wherein the first primer and the blocker polynucleotide compete with each other to hybridize to a common subsequence adjacent to an attB integration site within the orfX sequence. Hybridization of the blocker polynucleotide is favored when the insertion polynucleotide is not present, and hybridization of the first primer is favored when the insertion polynucleotide is present (e.g., a SCCmec complex comprising a mecA gene).

In some embodiments, the compositions include a plurality of first and second primers and/or a plurality of blocker polynucleotides, for example, for performing multiplex PCR.

The compositions can further include a target polynucleotide sequence (e.g., a genomic nucleic acid sequence from a host cell), nucleotide bases (dNTPs including dATP, dCTP, dGTP, dTTP, dUTP), polymerases, and appropriate reaction buffers, salts and metal ions. In some embodiments, the polymerase is a Taq polymerase, although any thermostable polymerase or DNA polymerase suitable for nucleotide sequence amplification or DNA extension reactions can be included. Thermostable polymerases are well known in the art and are readily commercially available (for example, from New England Biolabs, Ipswich, Mass.; Promega, Madison, Wis.; Stratagene, La Jolla, Calif.; Roche Applied Science, Indianapolis, Ind.). In some embodiments, the compositions further include one or more detection probes for detecting amplification of an amplicon, for example, for real-time amplification detection.

Kits

The invention further provides kits comprising the first and second primers, one or more blocker polynucleotides and optionally detection probes, as described above for the compositions and methods. The kits optionally can further comprise a control target polynucleotide, for example, a control genomic sequence from a host cell known to have integrated or known not to have integrated an insertion polynucleotide. In addition, the kit can include amplification reagents, including nucleotides (e.g., A, C, G and T), a DNA polymerase and appropriate buffers, salts and other reagents to facilitate amplification reactions. In some embodiments, the kits further include one or more detection probes for detecting amplification of an amplicon, for example, for real-time amplification detection. In some embodiments, the kits include a plurality of first and second primers and/or a plurality of blocker polynucleotides, for example, for performing multiplex PCR. The kits can also include written instructions for the use of the kit to amplify and control for amplification of a target sample.

In some embodiments, the invention provides kits that include one or more reaction vessels that have aliquots of some or all of the reaction components of the invention in them. Aliquots can be in liquid or dried form. Reaction vessels can include sample processing cartridges or other vessels that allow for the containment, processing and/or amplification of Samples in the same vessel. In some embodiment, the kits further comprise a multiwell substrate (e.g., multivessel strip, multivessel plate), for example, for concurrently amplifying from a plurality of target polynucleotides. Such kits allow for ready detection of amplification products of the invention into standard or portable amplification devices.

In some embodiments, the kits comprise vessels such as sample processing cartridges useful for rapid amplification of a sample as described in Belgrader, P., et al., Biosensors and Bioelectronics 14:849-852 (2000); Belgrader, P., et al., *Science*, 284:449-450 (1999); and Northrup, M. A., et al. "A New Generation of PCR Instruments and Nucleic Acid Concentration Systems" in PCR PROTOCOLS (Sninsky, J. J. et al (eds.)) Academic, San Diego, Chapter 8 (1998)).

EXAMPLES

The following examples are offered to illustrate, but not to limit the claimed invention.

Example 1

Detection of Methicillin-Resistant *Staphylococcus aureus* (MRSA) Using an SCCmec Junction Blocker Polynucleotide Real-time PCR (RT-PCR; 5'-nuclease assay) reactions were carried out to determine the presence or absence of an SCCmec integrated into the genomic DNA of MRSA and MSSA isolates at the insertion site. The reaction used two primers that hybridized to orfX sequences, a fluorescently-labeled probe and one of two blocker polynucleotides designed to accommodate sequence polymorphisms known to occur in the orfX region of *S. aureus* (below).

```
orfX forward primer (F1):
                                   (SEQ ID NO: 1)
5'-AGGGCAAAGCGACTTTGTATTC-3' orfX reverse primer (R11):
                                   (SEQ ID NO: 2)
5'-CTTATGATACGCTTCTCCTCGC-3'
```

Separate reactions were carried out in the presence of each of the following blocker polynucleotide sequences:

```
                                                 (SEQ ID NO: 12)
5'-CAGAATTTTTAGTTTTACTTATGATACGCCTCTCCTCGC-PO3-3'.

(SEQ ID NO: 13)
5'-TAAAAAACTCCTCCGCTACTTATGATACGCTTCTCCTCGC-PO3-3'.
```

Figure 3:
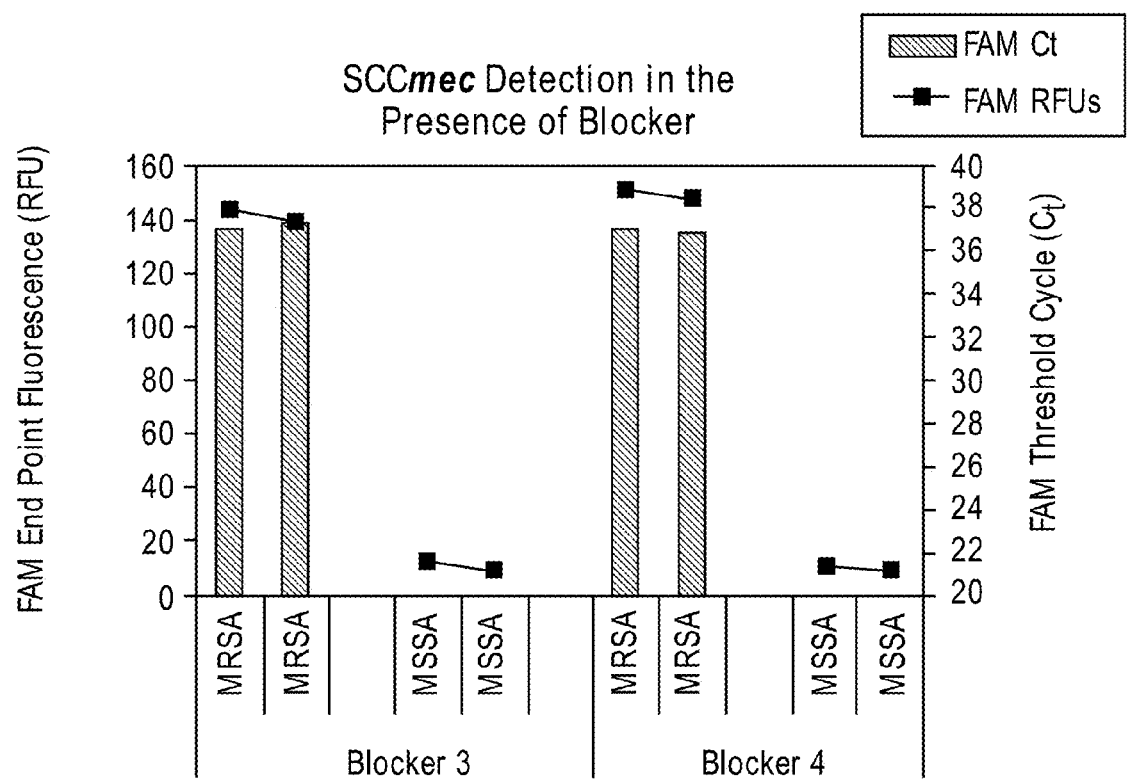
FIG. 3. The results of an experiment demonstrating the effect of two different blocker polynucleotides on the detection of methicillin-resistant *Staphylococcus aureus* (MRSA) and methicillin-sensitive *Staphylococcus aureus* (MSSA) using the 5'-nuclease assay. FAM end point fluorescence is indicated in relative fluorescence units (RFU).

The results are shown in Table 2 and in FIG. 3.

TABLE 2

| Protocol | S. aureus strain | FAM End point fluorescence (RFU) | FAM Threshold Cycle ($C_t$) |
|---|---|---|---|
| Blocker 3 | MRSA | 143.71 | 37.13 |
|  | MRSA | 138.95 | 37.39 |
|  | MSSA | 11.65 | ND* |
|  | MSSA | 8.59 | ND* |
| Blocker 4 | MRSA | 150.79 | 36.96 |
|  | MRSA | 147.83 | 36.89 |
|  | MSSA | 10.52 | N.D*. |
|  | MSSA | 9.64 | N.D*. |

*ND = $C_t$ not detected. The fluorescent signal did not cross the threshold during 45 cycles of real-time PCR indicating that the orfX amplicon was not detected.

As can be seen from the Table, a subsequence of the orfX region was amplified from MSSA strain genomic DNA in the absence of the blocker polynucleotide. However, the orfX subsequence was not amplified in when either of the two blocker polynucleotides were present in the reaction. A target within the orfX region was amplified and detected with a robust positive signal from MRSA genomic DNA in the presence or the absence of either blocker polynucleotide.

Example 2

Detection of orfX from MRSA and MSSA Genomic DNA in the Presence or Absence of an SCCmec Junction Blocker Polynucleotide An RT-PCR was carried out to determine the effect of a blocker polynucleotide on the amplification of an orfX amplicon from the host genomes of MRSA and MSSA strains. PCR reactions were carried out using forward and reverse primers that hybridized to orfX and the amplification was detected with a FAM-labeled probe (below).

```
orfX forward primer (F1):
                                           (SEQ ID NO: 1)
5'-AGGGCAAAGCGACTTTGTATTC-3' orfX reverse primer (R11):
                                           (SEQ ID NO: 2)
5'-CTTATGATACGCTTCTCCTCGC-3' orfX probe:
                                           (SEQ ID NO: 14)
5'-FAM-CGGCCTGCACAAGGACGTCTTACAACGTAG-Quencher 3'
```

Figure 4:
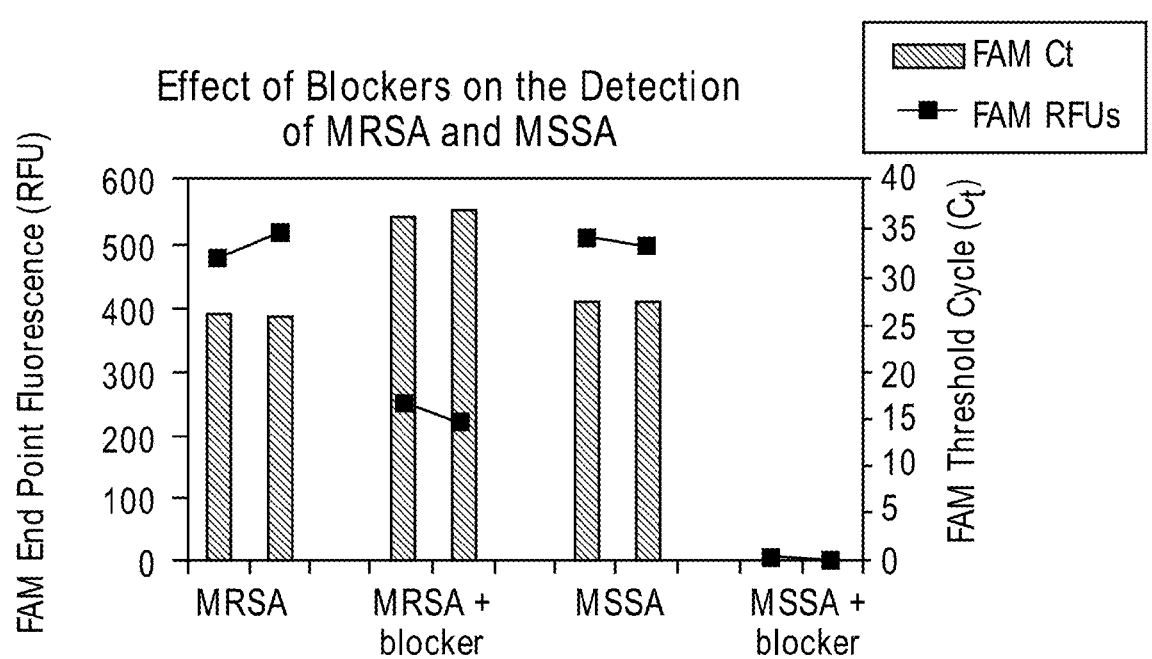
FIG. 4. The results of an experiment demonstrating the effect of the presence or absence of a blocker polynucleotide on the detection of MRSA and MSSA. FAM end point fluorescence is indicated in relative fluorescence units (RFU).

The results are shown in Table 3 and in FIG. 4.

TABLE 3

| S. aureus strain | Blocker | FAM End point Fluorescence (RFU) | FAM Threshold Cycle ($C_t$) |
|---|---|---|---|
| MRSA | − | 478.39 | 25.74 |
| MRSA | − | 517.99 | 25.55 |
| MRSA | + | 245.12 | 36.23 |
| MRSA | + | 220.29 | 36.58 |
| MSSA | − | 507.85 | 26.93 |
| MSSA | − | 493.96 | 26.93 |
| MSSA | + | 4.19 | ND* |
| MSSA | + | 1.72 | ND* |

*ND = $C_t$ not detected. The fluorescent signal did not cross the threshold within 45 cycles of real-time PCR indicating that the orfX amplicon was not detected.

As can be seen from Table 3, the orfX subsequence was not amplified from MSSA genomic DNA in the presence of the blocker polynucleotide. In the absence of the blocker, an orfX subsequence was amplified. The orfX subsequence was amplified with a robust positive signal from MRSA genomic DNA in the presence and absence of a blocker polynucleotide.

Example 3

Testing of Blocker GCG49

In this example, blocker GCG49 was tested for its ability to block amplification of target polynucleotide sequences (orfX) in 80 different clinical isolates of MSSA. The sequences of the orfX and attB regions of these 80 isolates were not known, but these isolates were chosen to represent a cross-section of S. aureus strains that might be encountered in the clinical environment.

The nucleotide sequence of MSSA strain ATCC 35556 in the orfX region is shown in Table 4, along with the blocker, primers and probe sequences.

TABLE 4

MSSA Target, Blocker GCG49 and PCR Primer Sequences

```
MSSA Target (segment of ATCC 35556)
ATTATCTCCTCATACAGAATTTTTTAGTTTTACTTATGATACGCCTCTCCTCGCATAATCTT

AAATGCTCTGTACACTTGTTCAATTAACACAACCCGCATCATTTGATGTGGGAATGTCATTT

TGCTGAATGAAGTGC(SEQ ID NO: 15)

Blocker GCG49 (highlighted)
CTCCTCATACAGAATTTTTTAGTTTTACTTATGATACGCCTCTCCTCGC
(SEQ ID NO: 6)

Probe MI80 (italics; mismatches in bold)
ccccGCTTCTCCACGCATAATCTTAAATGCTCT (SEQ ID NO: 16)

Primer R6 (double underline)
TACTTATGATACGCTTCTCC (SEQ ID NO: 10)

Primer (single underline)
CAATTAACACAACCCGCATCATTTGATGTGGG (SEQ ID NO: 17)
```

Procedure:

Crude extracts of DNA from 80 isolates of MSSA were obtained by first pure-streaking these bacterial strains in Petri plates contain an agar medium. A single, isolated colony from a given strain was picked up with an inoculating loop, and then suspended in one milliliter of molecular biology-grade water. This process was repeated for all 80 isolates. The tubes were capped, then heated to 95° C. for 10-15 minutes. After the solutions were cooled, these DNA extracts were centrifuged for at 10,000×g for 5 minutes to remove cellular debris. A several microliter aliquot of the DNA-containing supernatant was diluted 100-fold in a 10 mM Tris buffer (pH 8.3) containing 1 mM EDTA. This diluted aliquot of lysate was then used as the test DNA sample. The amount of DNA present in these samples was not quantified. Because of the simple method used for preparation the DNA quantity was certain to be varied from preparation to preparation. The DNA samples were then subject to real-time, quantitative PCR with or without the presence of Blocker GCG49.

Figure 5:
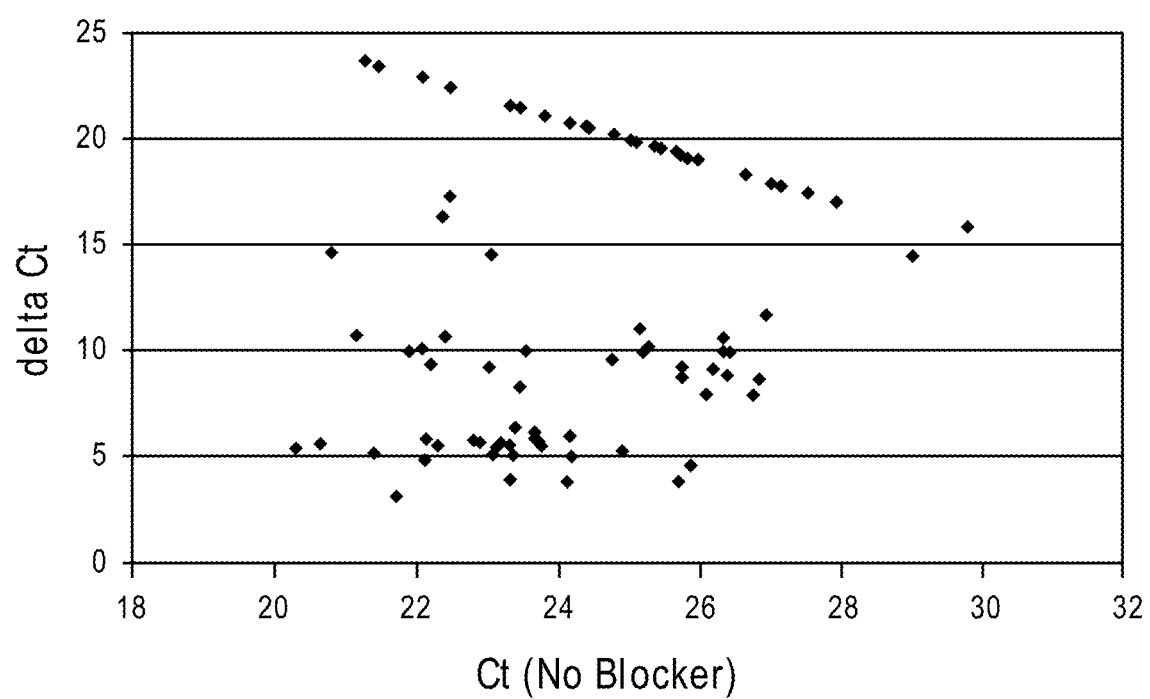
FIG. 5. The effect of Blocker GCG49 on 80 different clinical isolates of MSSA. Data plotted as the change in threshold cycle ($\Delta Ct$; $Ct_{with\ blocker}$-$Ct_{with\ blocker}$), for the blocked MSSA strain, versus the Threshold cycle (Ct) of the unblocked MSSA strains.

The results are depicted in FIGS. 5 and 6. In the absence of blocker polynucleotide GCG49 OrfX was amplified from the genomic DNA of all 80 tested MSSA strains. The Ct value observed for these RT-PCRs is proportional to the amount of DNA target present at the start of the reaction. The Ct value will be lower when a greater quantity of target DNA is present, and the $C_t$ will be higher when lower quantities of DNA are present, i.e. when higher quantities of DNA are present, the fluorescence will cross the detection threshold in fewer cycles than when a lesser amount of DNA is present. The C, values observed for these unblocked isolates ranged from 22 to 30. This suggests that the amount of genomic DNA present at the start of the reaction differed by as much as 256-fold from preparation to preparation.

Blocking is demonstrated by an increased $C_t$ value for the detection of the orfX subsequence, when blocker is present, as compared the $C_t$ observed in the absence of the blocker polynucleotide. This value, the delta $C_t$ ($C_t$ from PCR with blocker present—$C_t$ from PCR without blocker) indicates the effectiveness of the blocker polynucleotide against a given strain. However, the delta $C_t$ cannot be viewed as an absolute value because the quantity of starting material varied significantly from reaction to reaction.

For example, a lysate that has a $C_t$ of 30 in the absence of blocker and a $C_t$ of 45 in the presence of blocker, has a delta $C_t$ of 15. In this example a delta $C_t$ of 15 indicates complete suppression of the amplification of the mg subsequence because a Ct of 45 indicates the no amplification product was detect in 45 PCR cycles. If the starting Ct is 20 and the delta Ct is 15 this would not represent a complete suppression of the orfX signal but rather ~33,000-fold reduction.

The impact of the blocker polynucleotide was demonstrated in all of the isolates tested even though the efficency of blocker showed considerable variation across the 80 isolates. In the presence of the blocker polynucleotide, 35% of the isolates showed complete inhibition of the orfX amplification, 22% showed a 1000- to 16,000-fold reduction in orfX amplification, 15% showed a 64- to 1000-fold reduction in the orfX amplification and 28% showed an 8- to 64-fold reduction in the orfX amplification.

Published sequences of the orfX and attB regions of the *S. aureus* genome show that sequence polymorphisms exist between strains. Therefore, it is unlikely that a single blocker polynucleotide will be effective for all MSSA strains. Multiple blocker polynucleotides will be required to suppress the amplification of target sequences within orfX regions present in the range of the MSSA strains encountered. Therefore, a well-designed blocker polynucleotide is expected to have a spectrum of effectiveness against a range of existing strains, effectively blocking the amplification of orfX target sequences in a particular subset of strains with less complete suppression of orfX target sequences from other strains. Therefore, in certain cases, it will be useful to include a "cocktail" of two or more blockers to achieve blocking over a broad spectrum of polymorphisms in the target polynucleotide sequence associated with different *S. aureus* strains.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed:

1. A method for determining the presence or absence of an insertion polynucleotide at a junction site in a target polynucleotide sequence, wherein the junction site in the target polynucleotide sequence is spanned by a first target sequence on one side and a second target sequence on the other side, the first and second target sequences being contiguous when the insertion polynucleotide is absent, the method comprising:

contacting the target polynucleotide sequence with a first primer, a second primer, a blocker polynucleotide, a polymerase, and one or more nucleotide triphosphates and performing an amplification reaction, wherein:

(i) the blocker polynucleotide hybridizes to both contiguous first and second target sequences when the insertion polynucleotide is absent, (ii) the first primer hybridizes to a first region of the first target sequence independent of the presence of the insertion polynucleotide, the first region being proximal to the junction site, and (iii) the second primer hybridizes to a second region of the first target sequence, the second region being distal to the junction site, wherein the second primer is capable of priming synthesis of a portion of the first target sequence spanned by the first and second regions of the first target sequence, such that when the insertion polynucleotide is present at the junction site, the first and second primers support exponential amplification of the portion of the first target sequence spanned by the first and second regions of the first target sequence, and when the insertion polynucleotide is absent from the junction site, the blocker polynucleotide hybridizes to the contiguous first and second target sequences to block hybridization of the first primer to the first region so that amplification of the portion of the first target sequence spanned by the first and second regions of the first target sequence is inhibited, whereby the presence or absence of the insertion polynucleotide at the junction site in the target polynucleotide sequence is determined by the presence or absence of amplified portion of the first target sequence spanned by the first and second regions.

2. The method of claim 1, wherein the full length of the first primer hybridizes to the first region of the first target sequence competitively with the blocker polynucleotide.

3. The method of claim 1, wherein a portion of the first primer hybridizes to the first region of the first target sequence competitively with the blocker polynucleotide.

4. The method of claim 1, wherein first primer and the blocker polynucleotide each is substantially complementary to the first region of the first target sequence within the target polynucleotide sequence and the first primer has fewer mismatched nucleotides than the blocker polynucleotide relative to the first region of the first target sequence within the target polynucleotide sequence.

5. The method of claim 1, wherein the first primer is completely complementary to the first region of the first target sequence within the target polynucleotide sequence and the blocker polynucleotide carries at least one internal mismatch compared to the first region of the first target sequence within the target polynucleotide sequence.

6. The method of claim 1, wherein the blocker polynucleotide comprises a moiety at its 3'-end selected from the group consisting of phosphate and hexylamine.

7. The method of claim 1, wherein the blocker polynucleotide comprises at least one nucleic acid analog base.

8. The method of claim 1, wherein the nucleotide triphosphates are dNTPs.

9. The method of claim 1, wherein the polymerase is a DNA polymerase.

10. The method of claim 9, wherein the DNA polymerase is a Taq DNA polymerase.

11. The method of claim 1, wherein the method is performed in a multiplex format.

12. The method of claim 1, wherein amplification comprises polymerase chain reaction (PCR).

13. The method of claim 1, wherein amplification comprises real time (PCR).

14. The method of claim 1, wherein the insertion polynucleotide is at least 10 nucleotide bases in length.

* * * * *